June 28, 1955 R. L. BYRUM Plant Pat. 1,403
ROSE PLANT
Filed Oct. 21, 1954
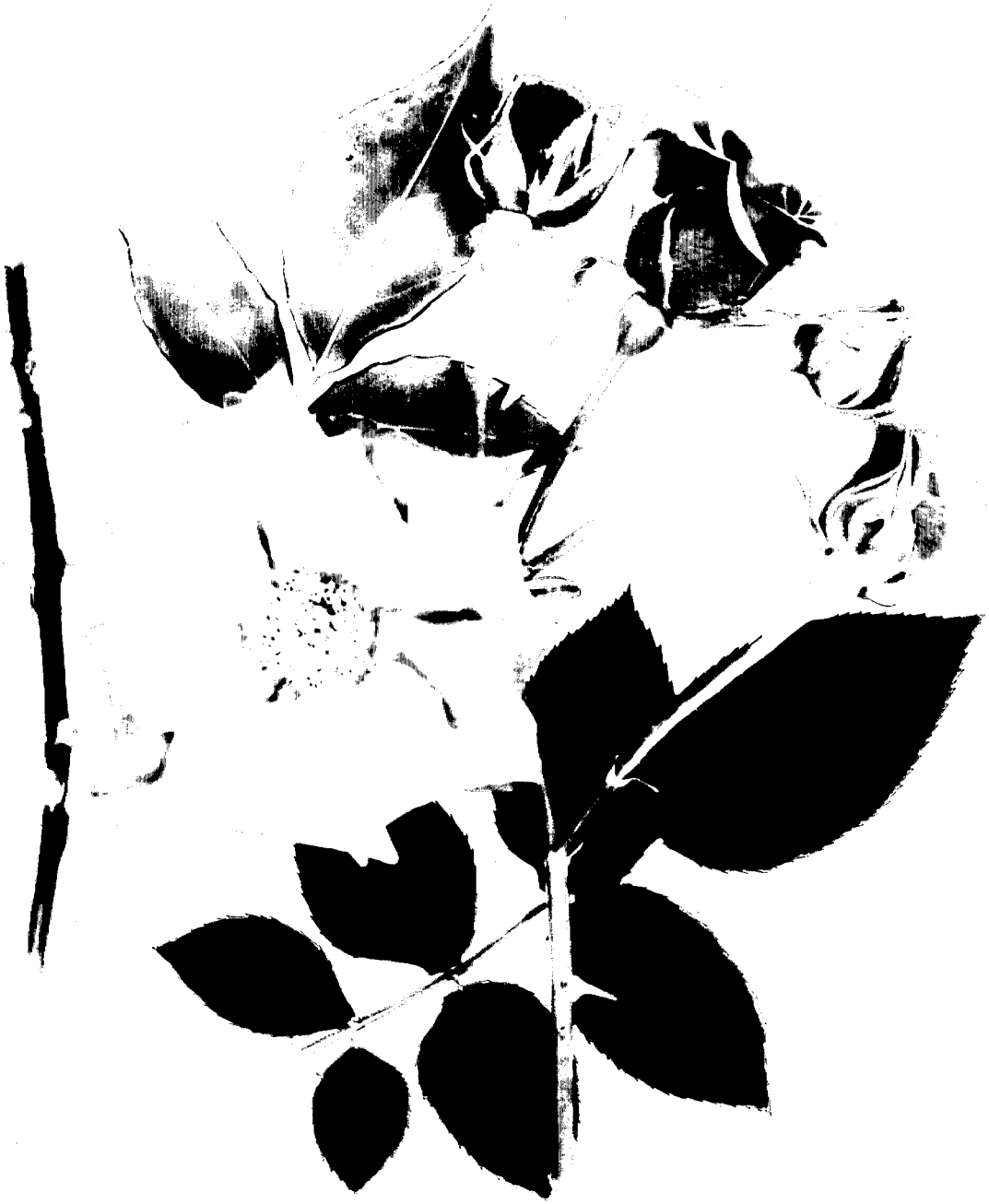
Inventor
R. L. Byrum
By: Robb & Robb
Attorneys United States Patent Office Plant Pat. 1,403
Patented June 28, 1955

1,403

ROSE PLANT

Roy L. Byrum, Richmond, Ind., assignor to Joseph H. Hill Company, Richmond, Ind., a corporation of Indiana Application October 21, 1954, Serial No. 463,840

1 Claim. (Cl. 47—61)

The present invention relates to a new and distinct variety of rose plant of the polyantha class, which was originated by me by crossing the variety "Garnette" (unpatented) with the variety "Sister Kenny" (Plant Patent No. 1,146.

The primary objective in making this cross was to produce a new rose variety having keeping qualities of its flowers comparable to the keeping qualities of the flowers of "Garnette," but at the same time, which bears flowers of a color comparable to those of "Sister Kenny." This objective was fully achieved, as evidenced by the fact that the flowers of my new variety are borne in clusters on relatively long stems, and have good keeping qualities, while the color of the flowers is a brilliant Red which is much brighter than the color of the flowers of "Garnette."

As compared with the parent variety "Garnette," which is a good forcer and good producer for cut flower production, and which bears very double flowers having good keeping qualities, my new variety clusters better than this parent, and the cluster flowers of the new variety are borne on longer stems. On the other hand, the parent variety "Sister Kenny" is not a good forcer for cut flower purposes, and its growth is much less uniform than that of my new variety.

Asexual reproduction of my new variety by grafting as performed at Richmond, Indiana, as well as by budding as performed at Wills Point, Texas, shows that the foregoing characteristics and distinctions come true to form and are established and transmitted through succeeding propagations.

The accompanying drawing shows typical specimens of the flowers, foliage and stems of my new variety in different stages of development and as depicted in color as nearly true as it is reasonably possible to make the same in a color illustration of this character.

The following is a detailed description of my new variety, with color terminology in accordance with Ridgway's Color Standards and Nomenclature (hereinafter abbreviated as "Ridgway"), Koster's Color Guide (hereinafter abbreviated as "Koster"), and Robert F. Wilson's Horticultural Colour Chart (hereinafter abbreviated as "Wilson"), as indicated:

Type: Greenhouse; bush; seedling.
Class: Polyantha.
Breeding: Seedling.
*Seed Parent.*—"Garnette."
*Pollen Parent.*—"Sister Kenny."
Propagation: Holds its distinguishing characteristics through succeeding propagations by both grafting and budding.

FLOWER

Locality where grown and observed: Richmond, Indiana, and Wills Point, Texas.
Flowers borne: Several to stem; in irregular clusters; on strong stems of medium length.
Quantity of bloom: Abundant, in greenhouse.
Continuity: Continuous.

Fragrance: Slight. Nature—tea.
Bud:
*Peduncle.*—Short; medium diameter; erect; medium strength. Bark — almost smooth. Color — Scheele's Green. Plate 860 (Wilson). Thorns—none. Prickles — numerous. Color — Uranium Green, Plate 63/3 (Wilson). Hairs — few. Color—Uranium Green, Plate 63/3 (Wilson).
*Before calyx breaks.* — Size — small. Form—short pointed; ovoid; with a conspicuous neck; with foliaceous appendages on the surface of the bud; with slender, entire foliaceous parts extending beyond the tip of the bud equal to ¼ or more of its length. Color—Scheele's Green, Plate 860 (Wilson).
*As calyx breaks.*—Color (outside of petal)—Currant Red, Plate 821/2 (Wilson), shading to Cardinal Red, Plate 822/3 (Wilson).
*As first petal opens.*—Size—medium small. Form—short pointed; ovoid. Color—outside of petal—Currant Red, Plate 821/3 (Wilson), lightly shaded with Cardinal Red, Plate 822/3 (Wilson). Inside of petal—Turkey Red, Plate 721 (Wilson).
*Opening.*—Opens up well in greenhouse; is normally affected by weather conditions, but without unusual characteristics.
Bloom:
*Size (when fully open).*—Medium small; from 2 inches to 3 inches.
*Petalage.*—Semi-double (in 2 or sometimes 3 rows); from 12 to 14 petals; arranged irregularly.
*Form.*—High-centered and globular at first, becoming flat-open; petals being at first tightly rolled outward, but becoming very loosely rolled outward later at maturity.
Petals: Moderately thick; leathery. Inside—satiny. Outside—satiny.
*Shape.*—Outside petals—obovate, with apex obtuse. Intermediate petals—obovate, with apex obtuse. Inside petals—obovate, with apex obtuse.

This description of a newly opened flower was made from a rose grown in a greenhouse in the month of August, at Richmond, Indiana:

Color:
*Outside petal.*—outside surface—Rose Red, Plate 724 (Wilson). Inside surface—Cherry Red, Plate 722 (Wilson).
*Intermediate petal.*—Outside surface—Rose Red, Plate 724 (Wilson). Inside surface—Cherry Red, Plate 722 (Wilson).
*Inner petal.*—Outside surface—Rose Red, Plate 724 (Wilson). Inside surface—Cherry Red, Plate 722 (Wilson).

This description was made from a rose that was open for 3 days in a greenhouse in the month of August, at Richmond, Indiana:

Color:
*Outside petal.*—Outside surface—Cherry, Plate 722/3 (Wilson). Inside surface—Turkey Red, Plate 721/3 (Wilson).
*Intermediate petal.*—Outside surface—Cherry, Plate 722/3 (Wilson). Inside surface—Turkey Red, Plate 721/3 (Wilson).
*Inner petal.*—Outside surface—Cherry, Plate 722/3 (Wilson). Inside surface—Turkey Red, Plate 721/3 (Wilson); some petals have White stripe through center.
Behavior: Persist in greenhouse; affected normally by weather, but without unusual characteristics; petals fade from Tyrian Rose, Plate 24/1 (Wilson) at outside petals, through Tyrian Rose, Plate 24/2 (Wilson) and Tyrian Rose, Plate 24/3 (Wilson) at center of bloom.

Flower longevity: Cut roses grown in greenhouse and kept at living-room temperatures—5 or 6 days in May.

General color effect:

*Newly open flower.*—Turkey Red, Plate 721/1 (Wilson).

*3-days open.*—Tyrian Rose, Plate 24 (Wilson).

PLANT

Foliage:

*Leaves.*—Compound of 5 to 7 leaflets; abundant; medium large; moderately heavy; leathery.

*Leaflets.*—Shape—ovoid. Apex—acute. Base—round. Margin—simple serrate.

*Color.*—Mature: upper surface—near Spinach Green, Plate 0960 (Wilson); under surface—Bice Green, Plate XVII (Ridgway). Young: upper surface—near Victoria Lake, Plate I (Ridgway); under surface—Near Victoria Lake, Plate I (Ridgway).

*Rachis (the supporting stem of the compound leaf).*—Medium light. Upper side—grooved. Under side—smooth; prickly.

*Stipules.*—Short; very narrow; with very short points turning out at an angle of less than 45°.

Growth:

*Habit.*—Bush; upright; much-branched.

*Growth.*—Free; vigorous.

*Canes.*—Medium diameter.

*Main stems.*—Color—some Spinach Green, Plate 75 (Koster), overlaid with Van Dyck Brown, Plate 96 (Koster); others entirely Van Dyck Brown, Plate 96 (Koster). Thorns—several; medium length; hooked downward; with short, broad base. Color—Bistre, Plate 93 (Koster). Prickles—few. Color—Bistre, Plate 93 (Koster). Hairs—none.

*Branches.*—Color—Spinach Green, Plate 0960/1 (Wilson). Thorns—several; long; hooked downward; with short, narrow base. Color—Yellowish Green, Plate 73 (Koster). Prickles—few. Color—Yellowish Green, Plate 73 (Koster). Hairs—none.

*New shoots.*—Color—Lettuce Green, Plate 861 (Wilson). Thorns—several; medium length; hooked downward; with short, narrow base. Color—Chartreuse Green, Plate 663/1 (Wilson) at tip, changing to Pale Lilac Rose, Plate 34 (Koster) at base. Prickles—none. Hairs—none.

*Reproductive organs*

Stamens: Many; regularly arranged about pistils.

Filaments: Medium length; most with anthers. Color—Crimson, Plate 22/2 (Wilson).

Anthers: Small; all open at once. Color—Crimson, Plate 22/2 (Wilson).

Pollen: Abundant. Color—Yellow Ochre, Plate 07/2 (Wilson).

Pistils: Many.

Styles: Uneven; medium length; thin; bunched. Color—Chrysanthemum Crimson, Plate 824/3 (Wilson).

Stigma: Color—Pure White, Plate 1 (Koster).

Ovaries: Most enclosed in calyx, with a few protruding from calyx.

Sepals: Permanent; moderately short; spear-shaped. Color: inside—Scheele's Green, Plate 860 (Wilson), overlaid with White fuzz; outside—Scheele's Green, Plate 860 (Wilson).

I claim:

A new and distinct variety of rose plant of the polyantha class, substantially as herein shown and described, characterized particularly as to novelty by its good flower clustering habit and the relatively long flowering stems, the good keeping qualities of its flowers, and the brilliant Red general color tonality of its flowers.

No references cited